United States Patent [19]

Asano et al.

[11] Patent Number: 5,279,146

[45] Date of Patent: Jan. 18, 1994

[54] METHOD AND APPARATUS FOR REAL TIME MEASUREMENT OF PARTICULATE MATTER IN COMBUSTION GASES

[75] Inventors: Ichiro Asano; Kennosuke Kojima; Tokihiro Tsukamoto; Hiroji Kohsaka, all of Kyoto, Japan

[73] Assignee: Horiba Ltd., Kyoto, Japan

[21] Appl. No.: 926,593

[22] Filed: Aug. 5, 1992

[30] Foreign Application Priority Data

Aug. 17, 1991 [JP] Japan .................................. 3-231194

[51] Int. Cl.⁵ .......................................... G01N 15/00
[52] U.S. Cl. .................................. 73/28.04; 73/28.01; 422/83; 422/93; 436/53
[58] Field of Search .......................... 73/28.01, 28.04; 250/345; 422/83, 93; 436/53, 145

[56] References Cited

U.S. PATENT DOCUMENTS

| | | | |
|---|---|---|---|
| 4,256,964 | 3/1981 | Ishida et al. | 250/345 |
| 4,271,124 | 6/1981 | Specter | 422/83 |
| 4,449,816 | 5/1984 | Kohsaka et al. | 73/28.01 |
| 4,555,931 | 12/1985 | Amimoto et al. | 73/23.2 |
| 4,705,669 | 11/1987 | Tsuji et al. | 422/93 |
| 5,110,747 | 5/1992 | Pataschnick et al. | 73/28.01 |

FOREIGN PATENT DOCUMENTS 8000747  4/1980  World Int. Prop. O. ......... 73/28.04

Primary Examiner—Robert J. Warden
Assistant Examiner—Laura E. Collins
Attorney, Agent, or Firm—Price, Gess & Ubell

[57] ABSTRACT

A method and apparatus for measuring particulates in a combustion gas is accomplished by dividing the combustion gas into a first and second sample gas. The first sample gas is filtered to remove particulates to create a reference gas sample. A combustion furnace can heat both the reference gas sample and the sample gas to oxidize any particulates in the sample gas. A gas analyzer that is connected to the furnace can detect the gas components in, respectively, the reference gas sample and the sample gas, and a comparison of the detected results can determine the concentration of particulates.

18 Claims, 2 Drawing Sheets

METHOD AND APPARATUS FOR REAL TIME MEASUREMENT OF PARTICULATE MATTER IN COMBUSTION GASES

BACKGROUND OF THE INVENTION

1. Field of the Invention

The present invention relates to an apparatus for the continuous real time analysis of particulate matter in gases and, more particularly, for the quantitative determination of particulates in an exhaust gas from a diesel engine.

2. Description of Related Art

The analysis of particulates in gases has usually required the collection of the particulates in a filter and a subsequent weighing of the particulates by a precise weight balance. For example, in an appointed volume of a high temperature exhaust gas discharged from a diesel engine, the exhaust gases have been introduced into a gas passageway to collect particulates by means of a collecting filter positioned in the gas passageway. The filter is then weighed with a precision balance and, knowing the previous weight of the filter without the particulate material, a determination can be made of the quantity of particulates that exist in the predetermined volume of the exhaust gas. This provides a quantitative analysis on the basis of a difference between the filter weight before collection of the particulates and the filter weight after collecting the particulates.

However, problems have occurred in these procedures, since water s frequently a by-product in the combustion gas of the diesel engine, and as water can be absorbed on the filter to provide an error in measurement. That is, the weight of the water will be mistaken for particulate material. A solution to this problem has been to soak the filter at constant temperature and humidity for several hours prior to use so that the weight of the filter and the water both before and after collecting the particulates will be the same. Additional problems, however, exist in that a volatile HC component known as sof (soluble organic fraction), soluble in the usual organic solvents, C components called dry soot, sulfate, and the like, are frequently contained in the particulates and the sof components must be extracted with organic solvents, while the sulfate particulates must be extracted with distilled water or by an eluting solution for use in an ion chromatography. As can be readily determined, it takes a long time period to complete such a measurement and to resolve the problems. This also requires a fairly high skill level in the work staff with potentials for errors so that individual operators can provide different analytical results.

In addition, the filter in which the particulates have been collected must be removed from the gas passageway. Thus, a disadvantage occurs in that a continuous measurement, or a real time measurement, cannot be effectively obtained. Thus, the ability to measure the different particulates that would occur under different load levels on the engine becomes difficult to measure.

Attempts have been made to provide particulate mass monitors for detecting the change of mass when the particulates are collected on the filter, such as a change of the residence frequency of a pipe and the like. Additionally, a Hertridge-type smoke meter, in which light is incident upon the particulates to measure a transmittance of the light, has also been developed as an alternative method of continuously measuring the particulates in diesel engine combustion gases.

Problems still remain, however, in such methods, such as the sof components cannot be measured distinctly from the dry soot, and these alternative methods are insufficient to the more commonly used method of collecting by means of a filter and weighing the filter on a weight balance. Accordingly, the prior art is still seeking to improve the methods and systems for measuring particulates in a gas combustion source.

SUMMARY OF THE INVENTION

The present invention has been accomplished in view of the above problems in the prior art and solves these problems by providing means for the continuous measurement of particulate-carrying combustion gases by dividing the particulate-carrying gases into first and second representative sample gases. A filter can be positioned in one of the gas passageways carrying the first sample gas to remove particulates from this gas sample and to provide a representative reference sample relative to another passageway. The respective reference sample and gas sample are both subjected to high temperatures in a combustion furnace that retains the gases at a temperature high enough to oxidize the particulate matter in the sample gas. A flow control system can direct the respective reference gas and sample gas to a gas analyzer, such as an infrared analyzer, that has appropriate detectors for measuring constituent gases in each sample. For example, an infrared gas analyzer can be utilized to measure the concentration of $H_2O$, $CO_2$, and $SO_2$. Since the only difference between the reference gas and the sample gas is the particulate matter that has been oxidized in the sample gas, a relative comparison of the detected oxidized gases provides a convenient manner of determining the particular concentration of particulates.

As can be readily appreciated, a system for measuring particulates can be done essentially on a real time basis in a highly convenient manner that does not require significant operator skills. A computer circuit can directly convert the results from the gas analyzer to determine the concentrations of HC, C, and S in the sample gas as a result of a difference between the sample gas and the reference gas in the detected concentrations of $H_2O$, $CO_2$, and $SO_2$. Accordingly, the particulate components, such as sof, dry soot, and sulfate, can be quantitatively determined without requiring the extraction by filter solvents and the like. Since there is no requirement to use a precise balance and organic solvents, a highly accurate measurement can be achieved in an almost automatic manner without the requirement of skilled personnel, and the exhaust gas discharge from a diesel engine can be continuously measured so that the exhaust characteristics of the particulates during a transitional operation can be measured in real time.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

DESCRIPTION OF THE PREFERRED EMBODIMENTS

The following description is provided to enable any person skilled in the art to make and use the invention and sets forth the best modes contemplated by the inventors of carrying out their invention. Various modifications, however, will remain readily apparent to those skilled in the art, since the generic principles of the present invention have been defined herein specifically to provide a real time measurement of particulate matter with a gas analyzer.

Figure 1:
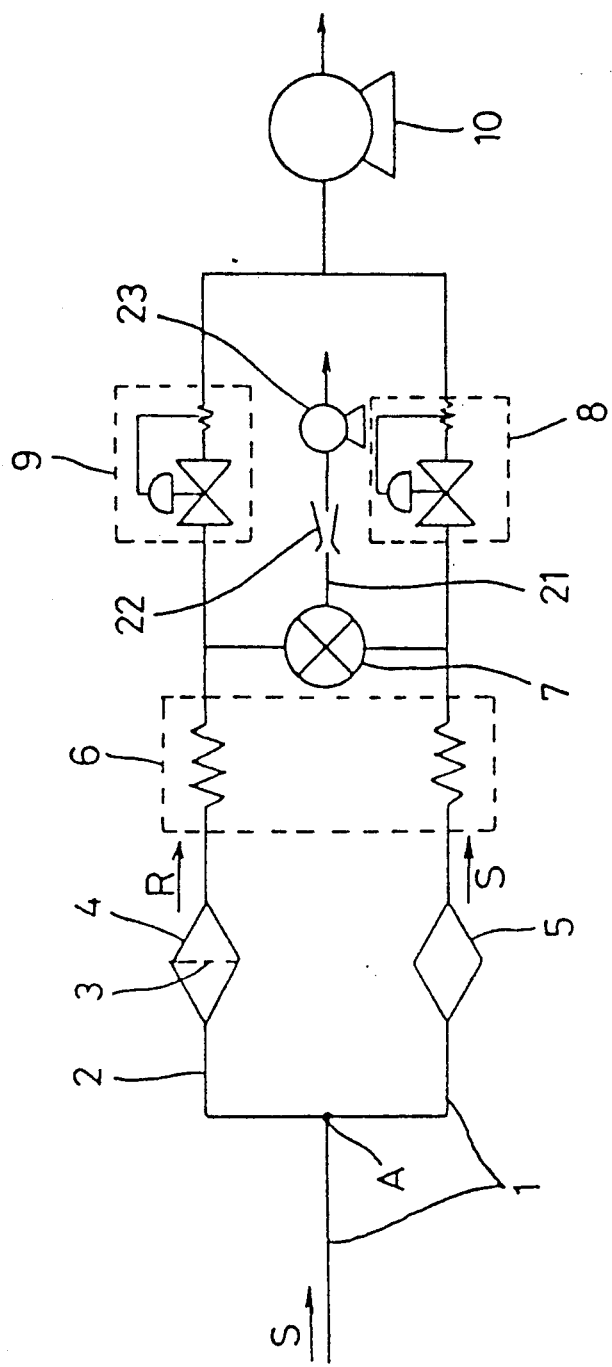
FIG. 1 is a schematic block diagram showing a system for analyzing particulates.

The preferred embodiments of the invention are described with respect to the drawings, wherein FIG. 1 is a schematic diagram showing an apparatus and system for the continuous analysis of particulates in accordance with the present invention.

In FIG. 1, a conduit can be connected to the exhaust of a diesel engine which constitutes the source S of the sample gas. This conduit 1 is then branched with a reference passageway 2 from a point A. The reference passageway 2 has a filter housing 4 in its passageway for housing a collecting filter 3 so that any particulates contained in the sample gas that travels through the passageway 2 will be collected on the filter 3. The collecting filter 3 can be made, for example, of quartz, Teflon TM, and a similar material that will not introduce any impurities into the gas. The sample passageway 1 also includes a housing 5, simulating the housing holder 4 in volume so that any dead space volume will be equal to that of the reference passageway 2 so that equal quantities of gas can be dealt with in a controlled manner. The combustion gas which passes through the filter 3 in sample passageway 2 is now the reference gas R, while the quantity of sample gas travelling through the housing 5 is the sample gas S carrying the particulate matter, which is to be determined by subsequent analysis.

Both of these passageways are connected to a heating combustion furnace 6, for example, an electric resistance furnace that is adapted to be able to keep a predetermined temperature therein for a predetermined time, which can be controlled through a subjective data inputting device (not shown). For example, the heat in the electric resistance furnace 6 can be maintained at 1000° C. for a sufficient time period during the passage of the respective gases to ensure that any particulate matter in the sample gas S will be oxidized into a gas, such as $H_2O$, $CO_2$, and $SO_2$.

Connected to the furnace 6 is a gas analyzer 7, such as an infrared gas analyzer, capable of differentially measuring the components in the combustion gas discharged from the furnace 6. A flow control circuit, including valves 8 and 9, can be used as a flow control device for the respective sample gas S and the reference gas R, so that they are synchronously supplied to the gas analyzer 7 without producing any time delay. For example, a mass flow controller can be used as a flow control valve system. In addition, a pump 10 can be used for a bypass of the infrared analyzer 7. The infrared analyzer itself can be attached to a pump 23 through a Venturi valve 22 for exhausting the measurement cells in the gas analyzer.

The control valves 8 and 9 provide a synchronously-supplied flow to the gas analyzer 7 with the sample gas S and the reference gas R without causing any delay. The control valves 8 and 9 are regulated so that the output of the analyzer 7 may be balanced.

In addition, the flow Venturi valve 22 and the exhaust gas pump 23 ensure that the exhaust flow rate from the gas analyzer 7 is constant. If the exhaust gas is sucked by means of the pump 23 so that the difference between the inlet pressure and the output pressure in the flow Venturi valve 22 may amount to the critical differential pressure or more, the flow rate of the gas flowing through the flow Venturi valve 22 is made constant (the critical flow rate).

Figure 2:
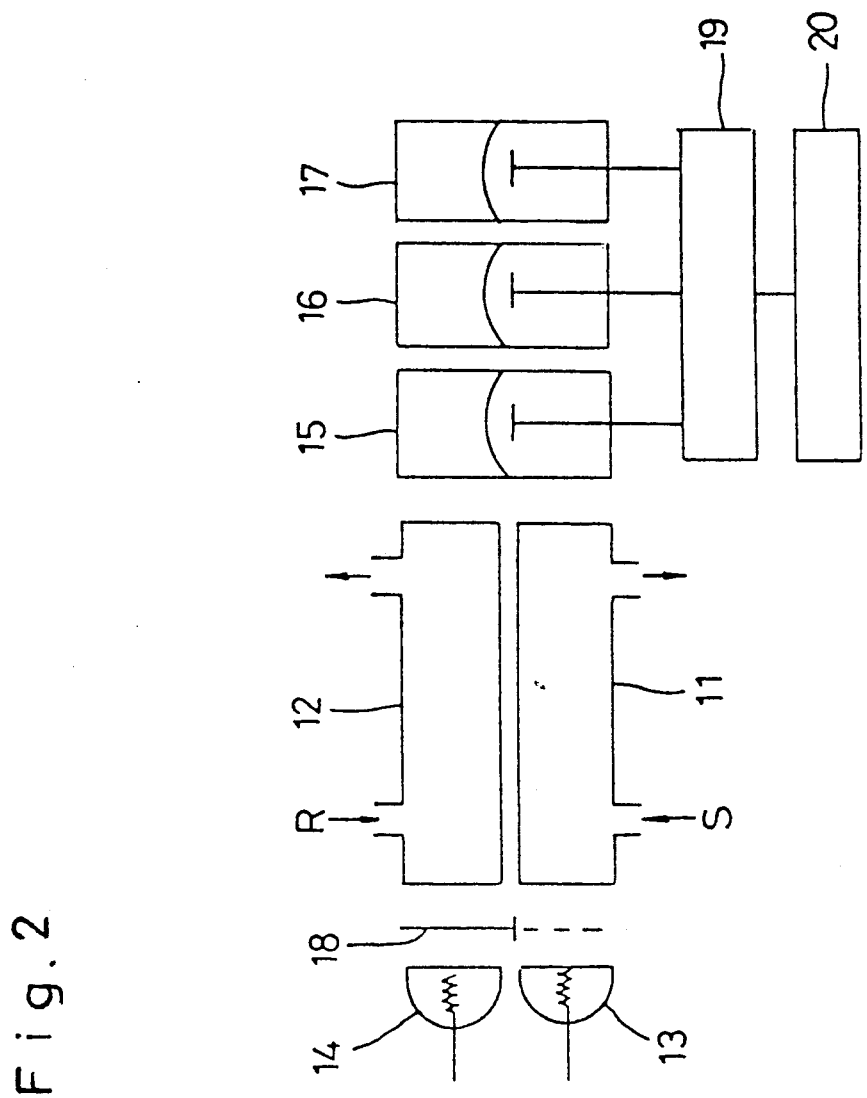
FIG. 2 is a schematic diagram showing an infrared gas analyzer for use in the system of FIG. 1.

Referring to FIG. 2, the gas analyzer 7 includes light sources 13 and 14, arranged on one side of the sample cell 11 and the reference cell 12 that are respectively connected to conduits for the reference gases R and S. On the other side of the sample cells, an $H_2O$ detector 15, a $CO_2$ detector 16, and an $SO_2$ detector 17 are arranged optically in series relative to the sample cell 11 and the reference cell 12 for simultaneously detecting a plurality of gases, such as $H_2$, $CO_2$, and $SO_2$. The sample cell 11 and the reference cell 12 are independent from each other to prevent any interference in the measurement cycle. A modulation chopper 18 is adapted to be rotated by means of a driving mechanism (not shown) to alternatively apply the light for the light sources 13 and 14 to the cells 11 and 12. The detected outputs from the respective detectors are fed to a preamplifier 19 to amplify these output signals, and these signals can be provided to a processing circuit 20, such as a computer circuit, for processing he outputs to determine the concentrations of the particulates in the gas sample.

A method of quantitatively determining the amount of particulates by such a gas analyzer will now be described. Referring to FIG. 1, a portion of the gas from the combustion source S will be divided into a reference passageway 2 at point A and into a sample passageway 1 at point A. The particulates contained in the reference gas passageway 2 are removed by a collecting filter 3, while the sample gas S passes through an equivalent volume space before being introduced into a heating combustion furnace 6. The reference gas R and the sample gas S are retained within the furnace 6 for a sufficient time period so that any particulate matter, such as CO, HC components, and sulfates, can be oxidized into a gas, such as $CO_2$, $H_2O$, and $SO_2$. With a diesel exhaust gas source, the heating combustion furnace can be heated and maintained at a temperature of approximately 1000° C. A gas flow controller, including flow control valves 8 and 9, can regulate the level of gas flow from the respective reference gas passageway and sample gas passageway to the gas analyzer 7.

As shown in FIG. 2, the reference gas is introduced into a sample cell 12, while the sample gas is introduced into a sample cell 11. Infrared rays from the light sources 13 and 14 are incident upon respective sample cells 11 and 12, with the infrared rays passing through these cells being absorbed within the cells to thereby enable the detection of any differences between $H_2O$, $CO_2$, and $SO_2$ in sample gas S and those in the reference gas R. These values can be detected by an $H_2O$ detector 15, a $CO_2$ detector 16, and an $SO_2$ detector 17 for their position on the opposite side of the respective sample cells 12 and 11. Since the sources are known, namely an exhaust gas from a combustion fuel, such as diesel fuel, the ratio of the number of atoms of the H components and the C components can almost be estimated. Accordingly, a chemical equation can be derived, wherein the concentration of carbon, C (dry soot), the concentration of HC (sof), and the concentration of S, can be set forth as components a, b, and c from the following chemical Equation (1). As a result, the concentration of $H_2O$, the concentration of $CO_2$, and the concentration of $SO_2$ in the sample gas can be determined as a relative difference between those constituents in the sample gas S and in the reference gas R.

$$aC+bCHx+cSO_4^{--}+\alpha O_2 \rightarrow (a+b)CO_2+(bx/2)H_2O+cSO_2+\beta O_2 \quad (1)$$

In the above-described Equation (1), a represents the concentration of C (dry soot), b represents the concentration of HF (sof), and c represents the concentration of sulfate. In addition, x represents the ratio of H to C in the number of atoms in sof preliminarily set depending upon the kind of fuel, and $\alpha$ and $\beta$ represent the concentration of oxygen that is in excess relative to a, b, and c.

The concentrations of sof, soot, and sulfates in the exhaust gas from the diesel engine can be separately determined from the ratio of H to C in number of atoms x, the concentration of $H_2O$, the concentration of $CO_2$, and the concentration of $SO_2$.

Diesel particulates include the soluble fractions (SOF) composed of hydrocarbons, carbon (dry soot), which is the insoluble fraction, and sulfates ($SO_1^{--}$). Provided that in a unit volume (1 m³, 20° C., 760 mmHg) carbon of a mol and hydrocarbons of b mol are oxidized and sulfates of c mol are converted into $SO_2$, the reaction is expressed by the following equation:

$$aC+bCHx+cS+\alpha O_2 \rightarrow (a+b)CO_2+(bx/2)H_2O+cSO_2+\beta O_2$$

wherein x represents the molar ratio of hydrogen to carbon (x=H/C) constructing the SOF; and $\alpha$, $\beta$ represent the mol numbers of $O_2$ excessive relatively to a, b, and c.

The concentration of $CO_2$, $H_2O$, and $SO_2$ generated is expressed by the following Equations (2), (3), and (4), respectively:

$$C\ CO_2 = 24.04(a+b)(1/m^3) \quad (2)$$

$$C\ H_2O = 24.04(bx/2)(1/m^3) \quad (3)$$

$$C\ SO_2 = 24.04c(1/m^3) \quad (4)$$

wherein 24.04 represents the volume of the ideal gas at 20° C. and 1 atmospheric pressure (l/mol).

In addition, the concentrations of particulates are expressed by the following Equations (5) to (7):

$$C\ D.S\ 12.011(a+b)(g/m^3) \quad (5)$$

$$C\ SOF = 12.011b + 1.008bx(g/m^3) \quad (6)$$

$$C\ SO_4 = 96.066c(g/m^3) \quad (7)$$

Provided that the unit of the concentration of particulates is mg/m³ and the unit of the concentration of gases generated is ppm, the following Equations (8), (9), and (10) are obtained from Equations (5), (6), and (7), respectively:

$$CD.S = \frac{12.011}{24.04} - \left( C\ CO_2 - \frac{2}{x} C\ H_2O \right)(mg/m^3) \quad (8)$$

$$C\ SOF = \frac{12.011 + 1.008 \cdot x}{24.04} \cdot \frac{2}{x} C\ H_2O\ (mg/m^3) \quad (9)$$

$$C\ SO_4 = \frac{32.066}{24.04} - C\ SO_2\ (mg/m^3) \quad (10)$$

The respective concentrations of particulates of dry soot, SOF, and sulfates can be calculated from the concentrations of gases generated by the use of Equations (8) to (10).

Since oxygen is contained in the usual exhaust gas from the diesel engine, it is not required to add oxygen. However, in a case where oxygen is insufficiently contained in the exhaust gas under special conditions, it is required to add oxygen for the combustion of particulates.

In the present preferred embodiment, a differential mass measurement-type infrared gas analyzer is used, but it should be clearly recognized that the present invention is not so limited, and that a fluid modulation-type multicomponent-type measurement infrared gas analyzer, for example, as disclosed in the specification and drawings of, for example, the Japanese Laid-Open Utility Model Application No. SHO 60-85105 may be used.

In accordance with the present invention, sof, dry soot, and sulfate can be separately and quantitatively determined without requiring the prior art pretreatment procedures of extraction of sof with solvents and the use of precision balances. Thus, a highly accurate measurement can be achieved in an almost automatic fashion by even unskilled technicians. In addition, the exhaust gas discharged from the diesel engine can be continuously measured so that exhaust characteristics of the particulates during transitional operation can be measured in real time.

Those skilled in the art will appreciate that various adaptations and modifications of the just described preferred embodiment can be configured without departing from the scope and spirit of the invention. Therefore, it is to be understood that, within the scope of the appended claims, the invention may be practiced other than as specifically described herein.

What is claimed is:

1. An apparatus for measuring particulates in a gas from a source, comprising:
   dividing means for dividing a particulate carrying gas from a source into a first sample gas and a second sample gas;
   means, connected to the dividing means, for removing particulates from the first sample gas to provide a first reference gas sample;
   combustion means, connected to the first and second sample gases, for heating the first reference gas sample and the second sample gas; and
   a gas analyzer connected to the combustion means to detect gas components in, respectively, the first reference gas sample and the second sample gas, whereby a comparison of detected results can determine the concentration of particulates.

2. The apparatus of claim 1 wherein the dividing means includes a pair of gas passageways.

3. The apparatus of claim 2 wherein the means for removing includes a housing chamber and a filter assembly a first gas passageway.

4. The apparatus of claim 3 further including a second gas passageway having a housing chamber of the same volume to ensure equal gas volumes.

5. The apparatus of claim 1 wherein the combustion means heats the first reference gas sample and the second sample gas at a temperature to convert the particulates in the second sample gas into gases.

6. The apparatus of claim 5 wherein the combustion means heats the first reference gas sample and the second sample gas to a temperature of at least 1000° C.

7. The apparatus of claim 5 wherein the combustion means heats the particulates to a temperature sufficient to oxidize the particulates.

8. The apparatus of claim 7 wherein the source is a diesel engine and the dividing means includes means for connection to a diesel engine.

9. The apparatus of claim 1 wherein the gas analyzer is an infrared analyzer.

10. The apparatus of claim 1 wherein the gas analyzer includes detectors for determining the concentrations of $H_2O$, $CO_2$, and $SO_2$.

11. The apparatus of claim 10 further including a computer circuit means for determining the concentrations of particulate sof, soot, and sulfate from the concentration of $H_2O$, the concentration of $CO_2$, and the concentration of $SO_2$ between the first reference gas sample and the second sample gas.

12. The apparatus of claim 11 wherein the combustion means heats the particulates to a temperature sufficient to oxidize the particulates.

13. A system for continuously measuring particulates in combustion gases, comprising:
   means for dividing combustion gases into first and second representative samples of particulate gases;
   means for filtering the first sample to remove particulates;
   means for heating a respective particulate-free first sample and a particulate-carrying second sample to oxidize the particulates in the second sample;
   means for detecting the amount of oxidized gases in each sample; and
   means for comparing detected oxidized gases in both samples to determine the amount of particulates in the second sample.

14. The system of claim 13 wherein the means for detecting includes an infrared analyzer.

15. The system of claim 13 wherein the means for heating includes a furnace for heating the respective first and second sample gases to at least 1000° C.

16. The system of claim 13, further including flow control means connected to the heating means for synchronously supplying, respectively, the first and second sample gases to the means for detecting without a time delay.

17. A method of measuring the particulates in a diesel combustion gas in a continuous manner as the diesel engine is operating, comprising the steps of:
   dividing a predetermined quantity of combustion gases into first and second representative samples;
   filtering the first sample to remove particulates;
   heating the first sample;
   heating the second sample to oxidize the particulates in the second sample to gases;
   detecting the amount of oxidized gases of the particulates in both the first and second sample; and
   determining the amount of particulates in the second sample by comparing the amount of oxidized gases of the first sample with the amount of oxidized gases in the second sample.

18. The method of claim 17 wherein the detecting step is performed with an infrared gas analyzer.

* * * * *